United States Patent [19]
Kumagae et al.

[11] Patent Number: 4,523,018
[45] Date of Patent: Jun. 11, 1985

[54] CERTAIN BIS(BENZOYL)PYRIDINE COMPOUNDS

[75] Inventors: Yojiro Kumagae, Osaka; Yasuhisa Iwasaki, Nara, both of Japan

[73] Assignee: Yamamoto Kagaku Gosei Co., Ltd., Osaka, Japan

[21] Appl. No.: 435,805

[22] Filed: Oct. 21, 1982

[30] Foreign Application Priority Data

Nov. 10, 1981 [JP] Japan .................. 56-178992

[51] Int. Cl.$^3$ .................. C07D 213/50; C07D 401/02
[52] U.S. Cl. .................. 546/315; 546/168; 546/187; 546/272; 546/273; 546/281; 546/314; 544/82
[58] Field of Search .................. 544/82; 546/187, 314, 546/315, 281

[56] References Cited

FOREIGN PATENT DOCUMENTS 1224590 3/1971 United Kingdom .................. 546/315
1416778 5/1974 United Kingdom .................. 546/116

OTHER PUBLICATIONS

Pratt et al., Chemical Abstracts, vol. 82, No. 25, Abst. No. 171,138y, Jun. 23, 1975.
Chemical Abstracts, Ninth Collective Index, vols. 76-85, Che. Substance, p. 23381 CS, (1972-1976), Pub. 1977.
Kumagae et al., Chemical Abstracts, vol. 99, No. 22, Abst. No. 185,058k, Nov. 28, 1983.

Primary Examiner—Alan L. Rotman
Attorney, Agent, or Firm—E. Frank McKinney; Paul S. Phillips, Jr.

[57] ABSTRACT

Chromogenic compounds of colorless or lightly colored form are disclosed having the following structural formula:

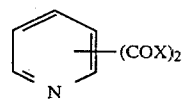

wherein X represents an optionally substituted aminophenyl, indolyl, julolidinyl, kairolyl, piperidinophenyl, pyrrolidinophenyl, morpholinyl, carbazolyl or indolizinyl radical. The compounds of this invention are eligible for use in pressure-sensitive and heat-sensitive record materials and manifold marking systems.

18 Claims, No Drawings

CERTAIN BIS(BENZOYL)PYRIDINE COMPOUNDS

This invention pertains to novel chromogenic compounds which can give intense colors when they are contacted with electron accepting co-reactant material. The invention also pertains to a process for production of the novel chromogenic compounds. More specifically, this invention relates to chromogenic compounds eligible for use in pressure sensitive or heat-sensitive mark-forming record systems. Such systems are improved by use of these compounds. As used in mark-forming systems, marking in desired areas on support webs or sheets may be accomplished by effecting localized reactive contact between the chromogenic material and the electron accepting material on or in such a web or sheet, such material being brought thereto by transfer or originally there in situ, the desired reactive contact forming colored images in the intended image-marking areas.

The chromogenic compounds of this invention have the following formula:

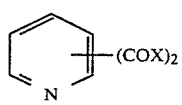
(I)

wherein X is:

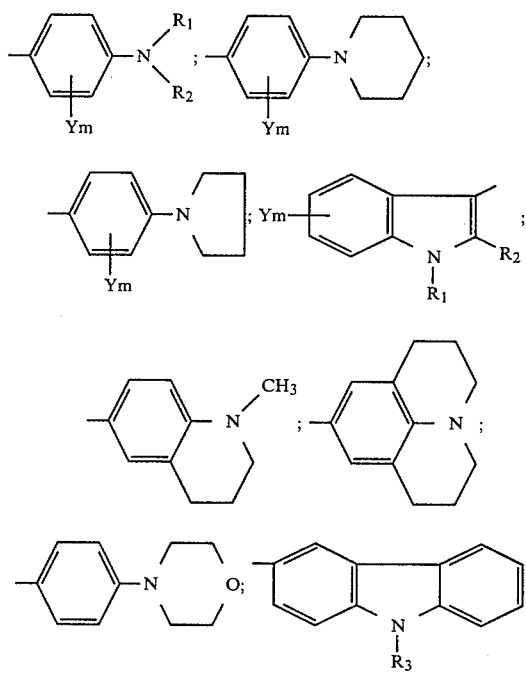

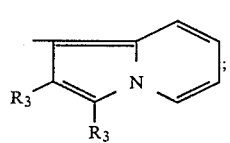

Y is lower alkyl, substituted lower alkyl, lower alkoxy, substituted lower alkoxy, lower dialkylamino, phenyl, substituted phenyl, benzyl, substitued benzyl, halo, a fused benzene ring or a substituted fused benzene ring; m is an integer of 0 to 4; $R_1$ and $R_2$ are alkyl of 1 to 8 carbon atoms, substituted alkyl of 1 to 8 carbon atoms, phenyl, substituted phenyl, benzyl, substituted benzyl or cycloalkyl of 5 to 6 carbon atoms; and $R_3$ is lower alkyl or phenyl.

As used herein the terms "lower alkyl", "lower alkoxy" and "lower dialkylamino" denote saturated acylic groups having from 1 to 4 carbon atoms which may be straight or branched. Lower alkyl can be, for example, methyl, ethyl, n-propyl, isopropyl or butyl. Lower alkoxy can be, for example, methoxy, ethoxy or isopropoxy. Lower dialkylamino can be, for example, dimethylamino, diethylamino, disopropylamino or dibutylamino. The substituent radicals of the term "substituted" denotes lower alkyl, halogenated lower alkyl, lower dialkylamino, lower alkoxy, halogen or cyano. The term "halogen or halo" denotes chloro, fluoro, bromo or iodo.

Compounds of formula (I) in which the (COX) groups are located in adjacent positions on the pyridine nucleus (hereinafter ortho compounds) are prepared by treating leuco compounds represented by formulae (II), (III), (IV) or (V), wherein X has the given meaning, with acetic anhydride followed by an oxidizing agent such as, for example, ferric chloride, chromate compounds or bichromate compounds.

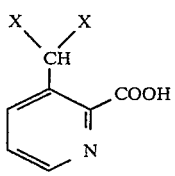
(II)

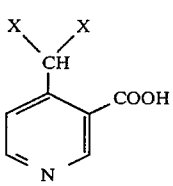
(III)

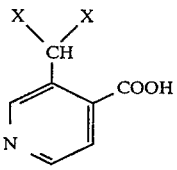
(IV)

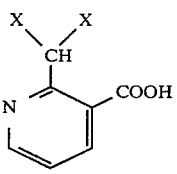
(V)

Compounds of formula (I), other than the ortho compounds, are prepared by reacting pyridine carboxylic acid halides represented by formula (VI),

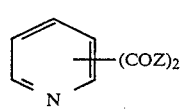
(VI)

with a compound represented by formula (VII),

X-H (VII)

wherein Z is chlorine or bromine and X has the meaning given, in an organic solvent such as, for example, chloroform, carbon disulfide, dichloroethane, chlorobenzene or dichlorobenzene, in the presence of a catalyst of the Friedel-Crafts type such as, for example, aluminum chloride or ferric chloride.

The chromogenic diketopyridine compounds of formula (I) are colorless or lightly colored and stable to atmospheric exposure. When these compounds are brought into contact with acidic (electron accepting) material they characteristically form a deep yellow, orange, or reddish-orange color and these colored products are very light stable. Eligible acidic, or electron acceptor materials include, but are not limited to, acid clay substances such as attapulgite, bentonite and montmorillonite and treated clays such as silton clay as disclosed in U.S. Pat. Nos. 3,622,364 and 3,753,761, phenols and diphenols as disclosed in U.S. Pat. No. 3,539,375, aromatic carboxylic acids such as salicylic acid, metal salts of aromatic carboxylic acids as disclosed in U.S. Pat. No. 4,022,936 and acidic polymeric material such as phenol-formaldehyde polymers as disclosed in U.S. Pat. No. 3,672,935 and oil-soluble metal salts of phenol-formaldehyde polymers as disclosed in U.S. Pat. No. 3,732,120. Thus, the diketopyridine compounds of this invention are useful as color formers in recording materials such as, for example, pressure-sensitive copying paper, thermally-responsive record material, electro heat-sensitive recording paper and thermal ink.

Pressure-sensitive copying paper systems provide a marking system of disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation, preferably comprises microcapsules containing liquid solvent solution. The microencapsulation process utilized can be chosen from the many known in the art. Well known methods are disclosed in U.S. Pat. Nos. 2,800,457, 3,041,289, 3,533,958, 3,755,190, 4,001,140 and 4,100,103. Any of these and other methods are suitable for encapsulating the liquid solvent containing the chromogenic compounds of this invention.

The chromogenic diketopyridine compounds of this invention are particularly useful in pressure-sensitive copying paper systems which incorporate a marking liquid comprising a vehicle in which is dissolved a complement of several colorless chromogenic compounds each exhibiting its own distinctive color on reaction with an eligible acidic record material sensitizing substance, the ink yielding an apparent substantial black on such sensitized record material. Such marking liquids are disclosed in U.S. Pat. No. 3,525,630.

Thermally-responsive record material systems provide a marking system of color-forming components which relies upon melting or subliming one or more of the components to achieve reactive, color-producing contact. The record material includes a substrate or support material which is generally in sheet form. The components of the color-forming system are in a contiguous relationship, substantially homogeneously distributed throughout a coated layer material deposited on the substrate. In manufacturing the record material, a coating composition is prepared which includes a fine dispersion of the components of the color-forming system, polymeric binder material, surface active agents and other additives in an aqueous coating medium.

The chromogenic diketopyridine compounds of this invention are useful in thermally-responsive record material systems either as single chromogenic compounds or in mixtures with other chromogenic compounds. Examples of such systems are given in U.S. Pat. Nos. 3,539,375 and 4,181,771.

The following examples are given merely as illustrative of the present invention and are not to be considered as limiting. Unless otherwise noted all percentages and parts throughout the application are by weight.

The intermediates required for the preparation of the novel chromogenic compounds of this invention are classes of compounds readily obtained by procedures well known in the prior art.

EXAMPLE 1

Preparation of 2,6-bis(N-methyl-N-cyclohexyl-4'-aminobenzoyl)pyridine.

After a mixture of 100 ml. of dichloroethane, 4 grams of pyridine-2,6-dicarboxylic acid chloride and 5.7 grams of aluminum chloride was stirred at room temperature to effect disolution, 8 grams of N-cyclohexyl-N-methylaniline were added dropwise while the temperature of the reaction flask was maintained at 15°–20° C. by external water cooling. After stirring at room temperature for about 20 hours, the resulting product was discharged into 200 ml. of water, the mixture was made alkaline and subjected to steam distillation, whereby the solvent and unreacted materials were removed. The residue was extracted with 200 ml. of toluene. The toluene solution was washed with hot water, filtered and concentrated. The 3.5 grams of pale yellow product, 2,6-bis(N-methyl-N-cyclohexyl-4'-aminobenzoyl)pyridine, had a melting point of 168.5°–170.5° C. An organic solvent solution of the product produced a yellow color on silton clay and an orange color on a zinc salt of a phenol-formaldehyde novolak resin made by procedures described in U.S. Pat. No. 3,732,120. The product was subjected to elemental analysis. The molecular formula, the calculated analysis based on the molecular formula and the results found on analysis were as follows:

| | | C | H | N |
|---|---|---|---|---|
| Formula: $C_{33}H_{39}N_3O_2$ | Calculated | 77.75 | 7.73 | 8.25 |
| | Found | 77.67 | 7.65 | 8.13 |

EXAMPLES 2–17

In a similar procedure to Example 1, 16 additional chromogenic diketopyridine compounds of the formula

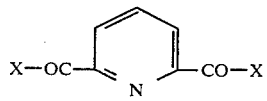
(VIII)

were prepared by reacting the appropriate starting material compound of formula (VII) with pyridine-2, 6-dicarboxylic acid chloride in dichloroethane in the presence of an aluminum chloride catalyst.

In Table 1 are listed Example Nos. 2–17, the corresponding identity of "X" in formula (VIII) of each Example and the melting point, color on silton clay and color on zinc salt of a phenol-formaldehyde novolak resin obtained with each Example.

TABLE 1

| Example No. | Identity of X in Formula (VIII) | Melting Point | Color on silton clay | Color on zinc salt of phenol-formaldehyde novolak resin |
|---|---|---|---|---|
| 2 | —C₆H₄—N[CH₃]₂ | 220.0–221.5° C. | Yellow | Orange |
| 3 | —C₆H₄—N[C₄H₉]₂ | 139.5–140.5° C. | Yellow | Orange |
| 4 | —C₆H₄—N(pyrrolidinyl) | 257.0–258.5° C. | Yellow | Orange |
| 5 | —C₆H₃(OCH₃)—N(pyrrolidinyl) | 218.0–219.5° C. | Yellow | Orange |
| 6 | —C₆H₃(N[CH₃]₂)—N[CH₃]₂ | 191.0–192.5° C. | Yellow | Reddish-Orange |
| 7 | —C₆H₃(OC₂H₅)—N(C₂H₅)—C₆H₄—CH₃ | 208.5–209.5° C. | Yellow | Orange |
| 8 | 2-methyl-1-ethylindol-3-yl | 231.0–232.5° C. | Yellow | Yellow |
| 9 | —C₆H₃(OC₂H₅)—[C₂H₅]₂ | 163.0–164.5° C. | Yellow | Yellowish-Orange |
| 10 | N-methyl-1,2,3,4-tetrahydroquinolin-6-yl | 242.5–244.0° C. | Yellow | Orange |

TABLE 1-continued

| Example No. | Identity of X in Formula (VIII) | Melting Point | Color on silton clay | Color on zinc salt of phenol-formaldehyde novolak resin |
|---|---|---|---|---|
| 11 | (tetrahydroquinoline fused structure) | 241.5–243.0° C. | Yellowish-Brown | Red |
| 12 | 4-morpholinophenyl | 231.5–232.5° C. | Yellow | Brownish-Yellow |
| 13 | 4-(N,N-dibenzylamino)phenyl | 177.5–179.5° C. | Yellow | Brownish-Yellow |
| 14 | 9-ethylcarbazol-3-yl | 214.5–215.5° C. | Yellow | Yellow |
| 15 | 1-methyl-2-phenylpyrrolo-pyridine | 133.0–134.5° C. | Yellow | Orange |
| 16 | 3-chloro-4-(N,N-dibutylamino)phenyl | 132.5–133.5° C. | Yellow | Orange |
| 17 | 3-methoxy-4-[N-methyl-N-(4-cyclohexylphenyl)amino]phenyl | 202.5–205.5° C. | Yellow | Orange |

Example 18

Preparation of 2,3-bis(N,N-dimethyl-4′-aminobenzoyl) pyridine.

A mixture of 35 grams of dimethylaniline and 20 grams of quinolinic acid anhydride were allowed to react at 80°–90° C. for about 4.5 hours in 50 ml. of acetic anhydride. The reaction mixture was made alkaline and extracted with 200 ml. of toluene at 85° C. The toluene solution was concentrated producing a solid deposit which was removed filtration and dried, yielding 23 grams of bis-7.7-(p-dimethylaminophenyl)-5.7-dihydrofuro [3.4-b]-pyridin-5-one (Compound IX). To a mixture of 20 grams of compound IX, 70 ml. of acetic acid and 6 grams of zinc powder was added 25 ml. of 35% hydrochloric acid dropwise over a period of 2 hours while the system was stirred under reflux. Refluxing was continued for an additional hour, the reaction mixture was made alkaline and the insoluble matter was filtered off. The filtrate was neutralized and the resulting solid deposit was removed by filtration washed with water and dried to yield 9.7 grams of bis (p-dimethylaminophenyl)-(3-carboxy pyridin-2-yl) methane (Compound X). A mixture of 5 grams of Compound X and 7.5 grams of acetic anhydride was stirred at 110° C. for 9 hours in an atmosphere of nitrogen. The reaction mixture was then discharged into ice water and the resulting mixture was made alkaline and extracted with toluene at 80°-85° C. The toluene solution was washed with hot water, concentrated and 0.5 grams of deposit was removed by filtration. To the deposit was added 10 ml. of water containing 1 ml. of 35% hydrochloric acid and 0.5 gram of ferric chloride and the mixture was reacted with stirring for 1 hour at 70° C. The resulting mixture was made alkaline with soda ash and extracted with toluene. The toluene extract was washed with hot water concentrated and filtered, yeilding 0.2 gram of product. The pale yellow product, 2,3-bis-(N,N-dimethyl-4'-aminobenzoyl) pyridine, melted with decomposition at 192.0°-194.0° C. An organic solvent solution of the product produced a yellow color on silton clay and a yellow color on a zinc salt of a phenol-formaldehyde novolak resin. The molecular formula, the calculated analysis based on the molecular formula and the results found on analysis were as follows:

|  |  | C | H | N |
|---|---|---|---|---|
| Formula: $C_{23}H_{23}N_3O_2$ | Calculated | 73.96 | 6.22 | 11.25 |
|  | Found | 73.97 | 6.28 | 11.13 |

EXAMPLE 19

Preparation of pressure-sensitive copying paper.

A solution of 0.5 gram of the chromogenic compound of Example 1 in 12 ml. of isopropylnaphthalene was microencapsulated substantially according to the procedure of U.S. Pat. No. 2,800,457. The microcapsule slurry was coated on a paper substrate and dried. The resulting microcapsule-coated sheet (termed the CB sheet) was coupled coated side to-coated side with an underlying receiving sheet (termed the CF sheet) bearing a coating comprising a zinc salt of a phenol-formaldehyde novolak resin or silton clay. The application of pressure to this CB-CF pair resulted in the production of an orange image on the CF sheet comprising a zinc salt of a phenol-formaldehyde novolak resin and a yellow image on the CF sheet comprising silton clay. These images were found to be high in light fastness.

EXAMPLE 20

Preparation of thermally-responsive record material.

A mixture of 3.5 grams of the chromogenic compound of Example 1, 15 grams of a 10% solution of polyvinyl alcohol in water and 6.5 grams of water was ground for 24 hours in a ball mill (Dispersion A). A mixture of 3.5 grams of 4,4'-isopropylidenediphenol, 150 grams of a 10% solution of polyvinyl alcohol in water and 65 grams of water was ground for 24 hours in a ball mill (Dispersion B). A mixture of 3 parts of dispersion A and 67 parts of Dispersion B was coated on paper and dried. When the resulting coated paper was locally heated with a hot pen or thermal head, a yellow color rapidly formed and was found to be high in light fastness.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A compound represented by the formula:

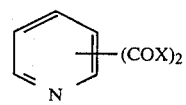

wherein X is:

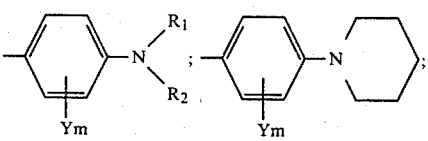

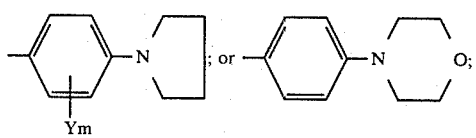

Y is: lower alkyl, lower alkoxy, phenyl, benzyl,, which is unsubstituted or substituted with lower alkyl, halogenated lower alkyl, lower dialkylamino, lower alkoxy, halogen or cyano, or is lower dialkylamino or halo; m is: an integer of 0 to 4; and $R_1$ and $R_2$ are: alkyl of 1 to 8 carbon atoms, of phenyl or benzyl, which is unsubstituted or substituted with lower alkyl, halogenated lower alkyl, lower dialkyamino, lower alkoxy, halogen or cyano, or are cycloalkyl of 5 to 6 carbon atoms.

2. The compound of claim 1 wherein X is

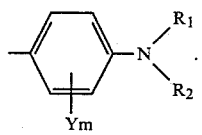

3. The compound of claim 2 wherein $R_1$ and $R_2$ are lower alkyl.

4. The compound of claim 3 wherein Y is halo.

5. The compound of claim 4 wherein Y is chloro.

6. The compound of claim 5 wherein $R_1$ and $R_2$ are butyl.

7. The compound of claim 6 wherein m is 1.

8. The compound of claim 6 wherein m is 0.

9. The compound of claim 3 wherein $R_1$ and $R_2$ are methyl and m is 0.

10. A compound represented by the formula:

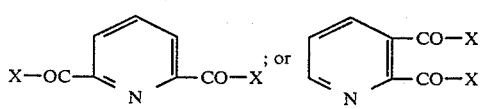

wherein X is:

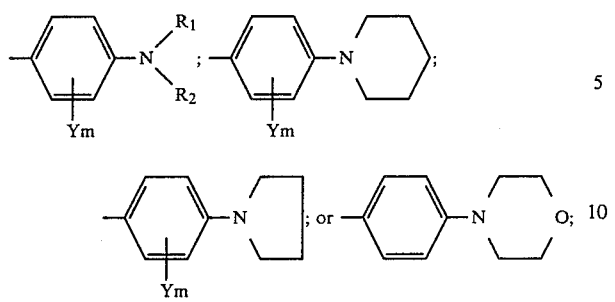
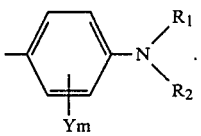

Y is: lower alkyl, lower alkoxy, phenyl, benzyl, which is unsubstituted or substituted with lower alkyl, halogenated lower alkyl, lower dialkylamino, lower alkoxy, halogen or cyano, or is lower dialkylamino or halo; m is: an integer of 0 to 4; and R₁ and R₂ are: alkyl of 1 to 8 carbon atoms, phenyl or benzyl, which is unsubstituted or substituted with lower alkyl, halogenated lower alkyl, lower dialkylamino, lower alkoxy, halogen or cyano, or are cycloalkyl of 5 to 6 carbon atoms.

11. The compound of claim 10 wherein X is

12. The compound of claim 11 wherein R₁ and R₂ are lower alkyl.
13. The compound of claim 12 wherein Y is halo.
14. The compound of claim 13 wherein Y is chloro.
15. The compound of claim 14 wherein R₁ and R₂ are butyl.
16. The compound of claim 15 wherein m is 1.
17. The compound of claim 15 wherein m is 0.
18. The compound of claim 12 wherein R₁ and R₂ are methyl and m is 0.

* * * * *